United States Patent [19]

Toyoshima et al.

[11] 4,349,682

[45] Sep. 14, 1982

[54] 2-(3-TRIMETHYLSILYLPROPYL)BENZO-THIAZOLE

[75] Inventors: Shigeshi Toyoshima, Tokyo; Ryuichi Sato, Gunma; Koichi Ito, Higashi-Kurume; Toshio Shinohara, Annaka; Yasushi Yamamoto, Takasaki, all of Japan

[73] Assignee: Shin-Etsu Chemical Co., Ltd., Tokyo, Japan

[21] Appl. No.: 186,211

[22] Filed: Sep. 11, 1980

[30] Foreign Application Priority Data

Sep. 17, 1979 [JP] Japan .................................. 54-119030

[51] Int. Cl.$^3$ ........................ C07F 7/10; A61K 31/425
[52] U.S. Cl. ..................................... 548/110; 424/184
[58] Field of Search ................. 548/152, 110; 424/270

[56] References Cited

U.S. PATENT DOCUMENTS

| | | | |
|---|---|---|---|
| 3,008,922 | 11/1961 | Lisanke | 548/110 |
| 3,692,798 | 9/1972 | Barcza | 548/110 |
| 3,947,465 | 3/1976 | Coll | 548/110 |

OTHER PUBLICATIONS

Lankelma et al., J. A.C.S., vol. 58, pp. 609–611, (1936).

*Primary Examiner*—David B. Springer
*Attorney, Agent, or Firm*—Toren, McGeady & Stanger

[57] ABSTRACT

The invention provides a novel compound 2-(3-trimethylsilylpropyl)benzothiazole having remarkable antitumor effects or, in particular, inhibiting growth of melanoma cells in test animals. The compound is synthesized by the ring-closing intramolecular dehydration condensation of 2-mercapto-($\gamma$-trimethylsilyl)-butyroanilide which in turn is obtained by the dehydrochlorination condensation of 2-aminothiophenol and $\gamma$-trimethylsilylbutyryl chloride in a polar solvent in the presence of an acid acceptor.

1 Claim, No Drawings

2-(3-TRIMETHYLSILYLPROPYL)BENZOTHIAZOLE

BACKGROUND OF THE INVENTION

The present invention relates to a novel organosilicon compound derived from benzothiazole and a method for the preparation thereof. The invention further relates to a method for preventing growth of tumor cells by medicating a patient with the above organosilicon compound as well as to a medicament containing the organosilicon compound as the effective ingredient.

In recent years, there have been undertaken intensive and extensive investigations to find compounds having anti-tumor or anti-cancer effects. Various kinds of organosilicon compounds also have been examined for the anti-tumor effect and several organosilicon compounds are reported to be effective. Among them, in particular, silatoran compounds are the most promising in preventing growth of tumor cells in test animals. Unfortunately, these compounds are not in actual therapeutic use because of the strong side effects caused by the toxicity thereof.

The inventors have conducted investigations of synthesizing a large number of novel organosilicon compounds and screening them from the standpoint of anti-tumor effectiveness with no undesirable side effects and, as a result, arrived at the establishment of the present invention.

SUMMARY OF THE INVENTION

The novel organosilicon compound of the present invention, of which the anti-tumor effectiveness has been established by the animal test, is 2-(3-trimethylsilylpropyl) benzothiazole, which is a novel organosilicon derivative of benzothiazole expressed by the structural formula

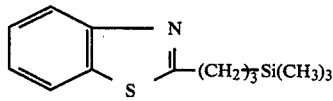

and is readily synthesized by the reaction of 2-aminothiophenol and γ-trimethylsilyl butyryl chloride.

This compound is effective in preventing growth of various kinds of tumor cells, for example, melanoma, transplanted in mice when the test animals are medicated with the compound as such or as diluted or dispersed in a suitable inert carrier.

DETAILED DESCRIPTION OF THE PREFERRED EMBODIMENTS

The organosilicon compound of the invention, 2-(3-trimethylsilylpropyl)benzothiazole expressed by the above given structural formula is a novel compound hitherto not known or not described in any prior art literatures. This compound is readily synthesized by the reaction of 2-aminothiophenol and γ-trimethylsilyl butyryl chloride in a polar solvent such as hexamethylphosphoric triamide in the presence of a hydrochloric acid acceptor such as triethylamine at a temperature of 50° C. or below to form an amide compound 2-mercapto-(γ-trimethylsilyl)butyroanilide as an intermediate compound, which is further heated at a temperature of 150° C. or higher to effect ring-closing intramolecular dehydration condensation into the desired bonzothiazole derivative. The reactions are shown by the following equations.

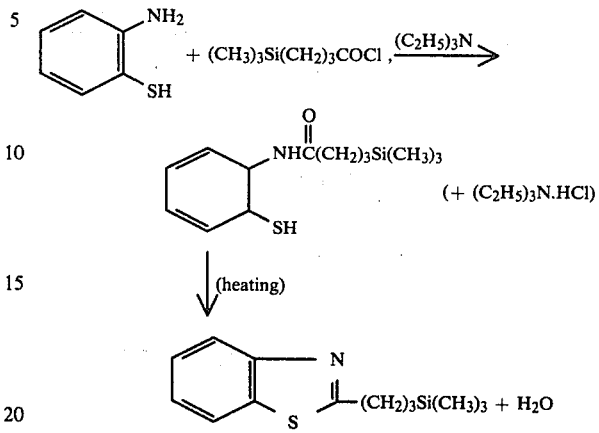

This compound is liquid at room temperature so that it can be injected as such to a tumor-bearing test animal or patient or may be used as diluted with or dispersed in a suitable inert carrier such as water, olive oil and the like.

In the following, synthetic preparation of the inventive compound and the effectiveness of the compound as an anti-tumor agent are described in detail by way of examples.

EXAMPLE 1

Into a reaction vessel were introduced 8.8 g (0.07 mole) of 2-aminothiophenol, 8.1 g (0.08 mole) of triethylamine and 40 ml of hexamethylphosphoric triamide to form a uniform solution with agitation. Into the above reaction mixture under cooling in a water bath were added 13.8 g (0.08 mole) of γ-trimethylsilylbutyryl chloride drop-wise with agitation whereby precipitation of triethylamine hydrochloride took place in the reaction mixture.

The reaction mixture was then, without separating the hydrochloride, heated up to a temperature of 150° to 160° C. where agitation was continued for further 3 hours to effect the intramolecular dehydration condensation of the amide compound into the desired benzothiazole derivative.

After completion of the reaction, the reaction mixture was washed with water to dissolve away the hydrochloride of triethylamine and the reaction product was extracted from the mixture with toluene. This toluene extract was subjected to purification by column chromatography with silica gel as the adsorbent. The thus purified product, weighing 13.9 g, had a refractive index of 1.5474 at 25° C. and the results of the elementary analysis, NMR absorption spectroscopy and infrared absorption spectroscopy undertaken with this product were as follows.

| | Elementary analysis: | |
| --- | --- | --- |
| | Found, % | Calculated as $C_{13}H_{19}NSSi$, % |
| C | 62.9 | 62.6 |
| H | 7.2 | 7.7 |
| N | 5.8 | 5.6 |
| S | 13.0 | 12.8 |

| -continued | | |
|---|---|---|
| Elementary analysis: | | |
| | Found, % | Calculated as $C_{13}H_{19}NSSi$, % |
| Si | 11.2 | 11.3 |

NMR spectral data: (with —Si(CH$_3$)$_3$ as the reference) 0.52–0.78 p.p.m. (—CH$_2$Si, 2H); 1.70–2.08 p.p.m. (—C—CH$_2$—C—, 2H); 3.08 p.p.m.

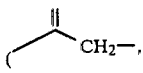

2H, triplet, J=7 Hz); 7.09–7.54 and 7.74–8.10 p.p.m. (aromatic protons, 4H).

Infrared spectral data: 1245 cm$^{-1}$; 830 cm$^{-1}$; and 850 cm$^{-1}$: —Si(CH$_3$)$_3$ 3060 cm$^{-1}$; 1590 cm$^{-1}$; 750 cm$^{-1}$; and 720 cm$^{-1}$: aromatic ring The above given analytical data all supported that the product compound was the desired 2-(3-trimethylsilylpropyl) benzothiazole. The yield of the product given above was about 80% of the theoretical value.

EXAMPLE 2

Twelve BDF 1 male mice in two groups, each composed of six, were transplanted subcutaneously with $2 \times 10^5$ cells of B-16 melanoma. The mice belonging to the first group were bred as such as a control. The mice belonging to the other group were treated by injecting 125 mg of 2-(3-trimethylsilylpropyl)benzothiazole synthesized as above once a day into the abdominal cavity for 14 days. All of the mice were killed 14 days after the transplantation of the tumor cells and the weight of the tumor in each of the killed mice was determined.

The inhibiting efficiency calculated by the following equation, in which A is the averaged tumor weight in the control group mice and B is the averaged tumor weight in the test group mice, was 86.2%.

$$\text{Inhibiting efficiency, \%} = \frac{A - B}{A} \times 100$$

For comparison, similar test was carried out with 5-fluorouracil at a dose rate of 27.5 mg once a day to give a value of the inhibiting efficiency of 72.3%.

What is claimed is:
1. 2-(3-trimethylsilylpropyl)benzothiazole.

* * * * *